US008945139B2

(12) United States Patent
Kemper et al.

(10) Patent No.: US 8,945,139 B2
(45) Date of Patent: Feb. 3, 2015

(54) BONE SCREW AND WASHER INSERTION TOOL

(75) Inventors: Jakob Kemper, Las Condes (CL); Nick Morfing, Nyack, NY (US); Michael Archdeacon, Cincinnati, OH (US); Henry Claude Sagi, Tampa, FL (US)

(73) Assignee: Stryker Trauma GmbH (DE)

( * ) Notice: Subject to any disclaimer, the term of this patent is extended or adjusted under 35 U.S.C. 154(b) by 66 days.

(21) Appl. No.: 13/589,593

(22) Filed: Aug. 20, 2012

(65) Prior Publication Data

US 2014/0052138 A1 Feb. 20, 2014

(51) Int. Cl.
*A61B 17/58* (2006.01)
*A61B 17/60* (2006.01)
*A61F 2/00* (2006.01)
*A61B 17/88* (2006.01)
*A61B 17/86* (2006.01)

(52) U.S. Cl.
CPC ......... *A61B 17/8894* (2013.01); *A61B 17/8872* (2013.01); *A61B 17/8875* (2013.01); *A61B 17/8695* (2013.01); *A61B 17/8635* (2013.01)
USPC .......................................... 606/104; 606/305

(58) Field of Classification Search
CPC ........... A61B 17/8875; A61B 17/8886; A61B 17/8891; A61B 17/8894
USPC .............................. 606/104, 305–308, 96, 99
See application file for complete search history.

(56) References Cited

U.S. PATENT DOCUMENTS

| | | | |
|---|---|---|---|
| 4,029,091 A | 6/1977 | von Bezold et al. | |
| 4,454,876 A | 6/1984 | Mears | |
| 4,800,874 A | 1/1989 | David et al. | |
| 5,354,292 A | 10/1994 | Braeuer et al. | |
| 6,004,353 A | 12/1999 | Masini | |
| 6,306,173 B1 | 10/2001 | Masini | |
| 6,340,362 B1 | 1/2002 | Pierer et al. | |
| 6,440,131 B1 | 8/2002 | Haidukewych | |
| 6,830,574 B2 | 12/2004 | Heckele et al. | |
| 7,074,203 B1 | 7/2006 | Johanson et al. | |
| 7,250,052 B2 * | 7/2007 | Landry et al. | 606/86 A |
| 2004/0106925 A1 | 6/2004 | Culbert | |
| 2005/0165401 A1 | 7/2005 | Pack | |

(Continued)

FOREIGN PATENT DOCUMENTS

FR 590290 A 6/1925
FR 2906126 A1 3/2008

(Continued)

OTHER PUBLICATIONS

Extended European Search Report for Application No. 1318088.3 dated Oct. 17, 2013.
Extended European Search Report for EP11157015.6 dated Aug. 4, 2011.
Stryker Trauma AG, Reduction Instruments, 2009.

*Primary Examiner* — Andrew Yang
(74) *Attorney, Agent, or Firm* — Lerner, David, Littenberg, Krumholz & Mentlik, LLP

(57) ABSTRACT

The insertion tool and pusher system of the present invention includes a bone screw having a head and a shaft. An annular washer is adapted to be mounted on the bone screw shaft. An insertion tool having a longitudinally extending shaft with an axial bore therethrough is provided for receiving the bone screw. The shaft has a first end with a washer retention surface surrounding the insertion tool cannulated shaft bore. The washer is held on the retention surface which positions the washer to receive the bone screw shaft. Pin-like spring elements are used to hold the washer in position. A plate is mounted on an outer surface at the first end of the inserter shaft, the plate having a bone contacting surface.

23 Claims, 10 Drawing Sheets

(56) References Cited

U.S. PATENT DOCUMENTS

| | | |
|---|---|---|
| 2009/0054903 A1 | 2/2009 | Falahee et al. |
| 2009/0275992 A1 | 11/2009 | Phan et al. |
| 2009/0275993 A1 | 11/2009 | Phan et al. |
| 2010/0094356 A1 | 4/2010 | Varela et al. |
| 2011/0190825 A1 | 8/2011 | Thalgott et al. |

FOREIGN PATENT DOCUMENTS

| | | |
|---|---|---|
| JP | 2004154480 A | 6/2004 |
| WO | 01/78616 A1 | 10/2001 |
| WO | 2009134888 A2 | 11/2009 |
| WO | 2009134893 A2 | 11/2009 |
| WO | 2009134896 A2 | 11/2009 |

\* cited by examiner

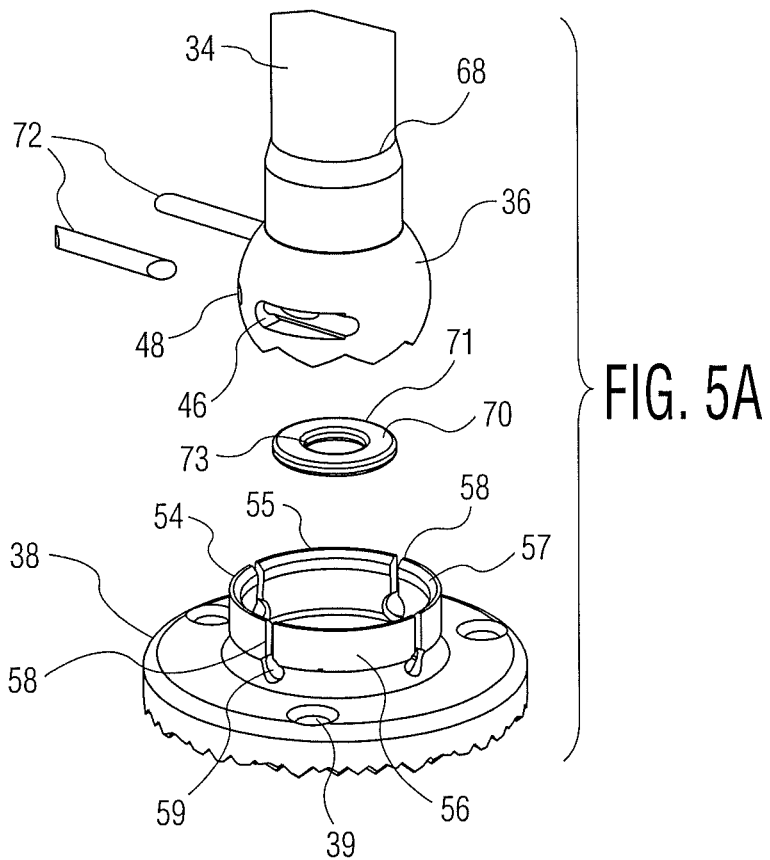
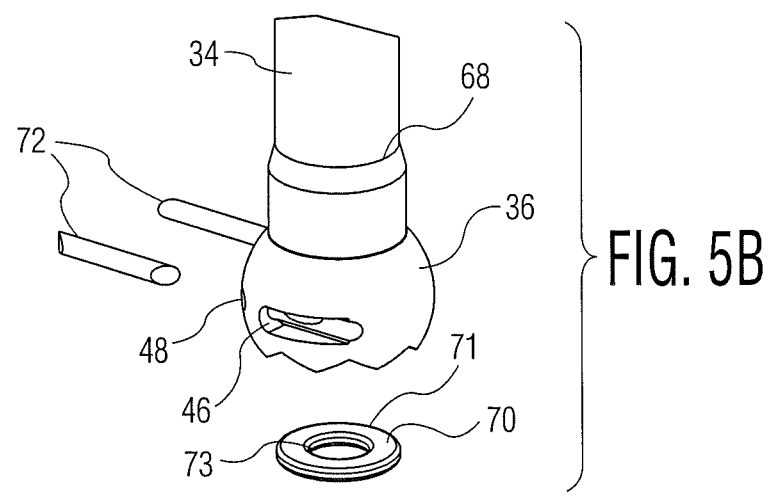

BONE SCREW AND WASHER INSERTION TOOL

BACKGROUND OF THE INVENTION

Bone fragment reduction and re-fixation are core parts of trauma surgery. Often bone fragments are manipulated and held in place with simple pushers, e.g., Ball Spike Pusher such as shown in FIG. 1. It is often desired to achieve refixation by inserting a screw into the bone fragment while still applying pressure on the reduction.

The pushers are often combined with so called spiked disks for footplates. FIG. 2 shows such a prior art pusher with a footplate. The footplate is a disk which is pivotably mounted on a part-spherical end of the pusher and includes bone contacting spikes. This allows for a constant interface with the bone while the pusher itself (with the handle) can be pivoted (swiveled) around the connection point to allow the application of force in a range of angles and to accommodate for the direction of the incision.

A typical problem is that the fracture reduction has to be held in place while trying to fix it, for example with a bone screw. The hole for the bone screw is prepared using a drill guide, which also has to be held in place.

Providing devices which holds the fragment and additionally simultaneously fix the fracture with a bone screw can cause several problems:

1) Space: The space in the surgical field and more specifically in the surgical window is very limited. To have one device for holding the fragment and another one for guiding the drill for the screw preparation and insertion next to each other is difficult.
2) Number of hands: If one of the surgeon's hands is required to keep pushing on a fragment and one hand to hold the drill, there is no free hand to use or manipulate a drill guide. An assistant physician needs to help out so the procedure gets more complicated, two people have to coordinate actions which is much more difficult than one physician pursuing a strategy to reduce the fracture.
3) Size of bone fragment: When pushing on a very small fragment, sometime there is not enough fragment-area adjacent the pusher to place a screw.

Also it should be mentioned that especially in regions with soft bone the screws should be inserted with a washer because otherwise the screw-head can sink into the bone too easily to apply compression to fix the fracture.

BRIEF SUMMARY OF THE INVENTION

The present invention uses a combination of a reduction pusher and a drill and screw insertion guide in one simple instrument. In addition, a washer can be preloaded into the device and stay in position during reduction and drilling through a cannulation in the device. When the screw is inserted the screw can be guided on the small diameter of the head of the screw and finally engages with the washer to pick it up before the head engages the bone. The device can also be used in conjunction with a footplate which pivots around the center of the connection of the sphere.

The insertion tool and pusher system of the present invention includes a bone screw having a head and a shaft. An annular washer is adapted to be mounted on the bone screw shaft. An inserter having a longitudinally extending shaft with an axial bore therethrough is provided for receiving the bone screw. The shaft has a first end with a washer retention surface surrounding the inserter shaft bore, the washer retention surface positions the washer to receive the bone screw shaft. A plate is mounted on an outer surface at the first end of the inserter shaft, the plate having a bone contacting surface. The inserter shaft has a leading end with an enlarged open recessed surface communicating with the shaft bore defining a seat for receiving the washer and having a resilient spring element for retaining the washer mounted thereon spaced towards the shaft leading end from the seat.

The system further comprises a washer loading device having a portion with an annular surface for supporting the washer, the loading device capable of expanding the resilient spring element upon movement into the enlarged open recessed surface of the inserter shaft. The plate bone contacting surface preferably has teeth thereon.

The insertion tool shaft includes a handle spaced along the inserter shaft away from the first end. The inserter shaft first end has a part-spherical outer surface with the plate mounted on the first end part-spherical outer surface. The plate has a bore with an angled surface which is rotatable on the part-spherical outer surface. The inserter first end has first and second crossbores extending along parallel first and second axis generally perpendicular to a longitudinal axis of the shaft. The first and second crossbores are adjacent the washer seat. A pin-like spring element extends through the first and second crossbores.

Other spring elements may be cylindrical spring pins. The aspects of the invention are provided by an insertion tool and pusher having a bone screw insertion system which includes a bone screw having a shaft and a head. The insertion tool provided has a cannulated shaft for receiving the bone screw and a first end having an annular recessed area surrounding an open end of the cannulated shaft. A bone contacting plate is pivotally mounted on an outer surface of the first end of the insertion tool. A driver, such as a screwdriver is provided for pushing the bone screw down the cannulated shaft and driving it into a bone. A washer having an aperture for receiving the bone screw shaft is mounted on the annular recessed area surrounding the cannulated bore and a resilient spring element engages the washer for maintaining the washer in the recessed area. The plate bone contacting surface and the insertion tool first end may have teeth thereon. A washer loading device is provided which has a portion with an annular surface for supporting the washer, the loading device capable of radially outwardly expanding the resilient spring element upon movement into an enlarged open bore of the inserter shaft adjacent the annular recessed area. Once the washer poses the spring element, such as spring pins, they expand inwardly capturing the washer and holding it on the annular surface.

The invention also includes a method for inserting a bone screw into bone which comprises providing a bone screw system which includes a bone screw having a shaft and a head. An insertion tool is provided having a cannulated shaft for receiving the bone screw and a first end having a flat recessed area surrounding an open end of the cannulated shaft. A bone contacting plate is pivotally mounted on an outer surface of the first end of the insertion tool and a driver is supplied for pushing the bone screw down the cannulated shaft and driving it into a bone. Prior to use a washer is inserted onto the recessed area of the insertion tool. A bone fracture is then compressed with the insertion tool bone contacting plate. A pilot hole is then drilled in the bone with a drill extending through the cannulated shaft while the bone is compressed. The bone screw is inserted through the insertion tool cannulated shaft into the drilled hole while maintaining the compression. The screw shaft is partially driven into bone and the washer is automatically picked up by the bone screw head prior to fully implanting the bone screw into the bone.

The combination of two devices into one with the additional feature of the preloaded washer allows the physicians to apply pressure in various angles to a fragment during drilling and screw insertion through one instrument.

BRIEF DESCRIPTION OF THE DRAWINGS

FIG. 5A is an enlarged view of the leading end of the pusher system shown in FIG. 5;

FIG. 5B is an embodiment of the present invention with the pivot plate eliminated;

DETAILED DESCRIPTION

Figure 1:
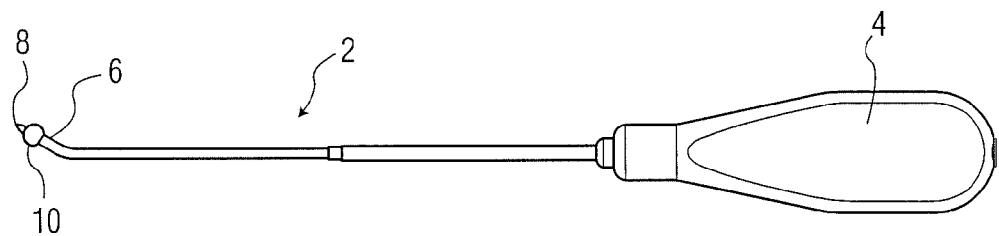
FIG. 1 shows a prior art pusher element designed to compress a fractured bone.

Referring to FIG. 1 there is shown a prior art pusher instrument generally denoted as 2 having a handle 4 and a leading end 6, including a spike 8 for engaging bone. The leading end 6 includes a part-spherical ball 10 upon which spike 8 is mounted and which bears against a bone fragment when spike 8 is embedded therein during pushing.

Figure 2:
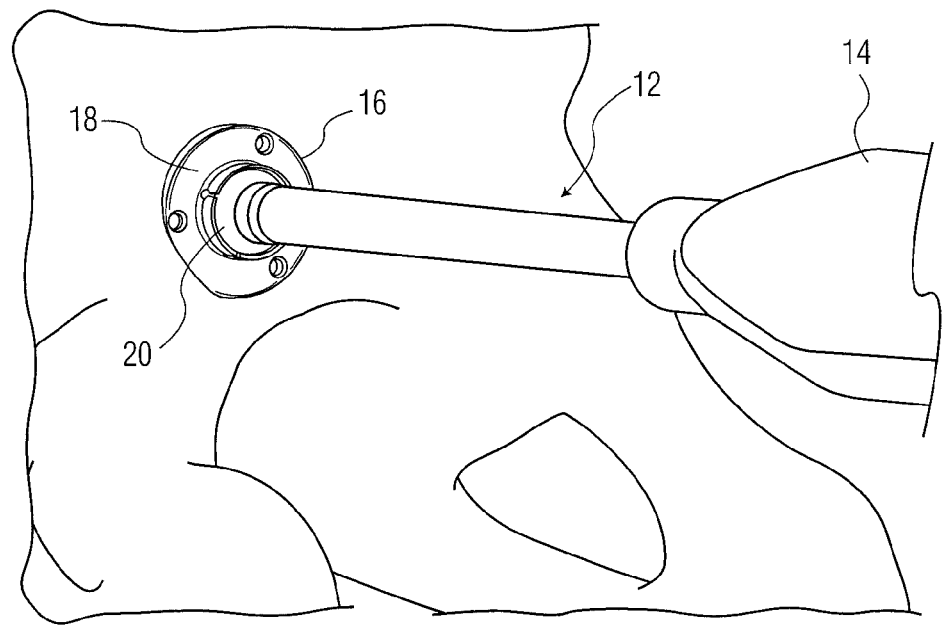
FIG. 2 is an alternate embodiment showing a prior art pusher capable of pivotal movement with respect to the bone during compression.

Referring to FIG. 2, there is shown a second prior art system generally denoted as 12, which includes a handle 14 and a leading end 16 which has a rotatable bone contacting plate 18 mounted on a part-spherical element 20. Plate 18 is sometimes referred to as a foot plate. Plate 18 has a part-spherical or angled inner surface which can rotate on the outer surface of part-spherical element 20 so that the tool can be angled and compression forces can be spread over a larger area.

Figure 3:
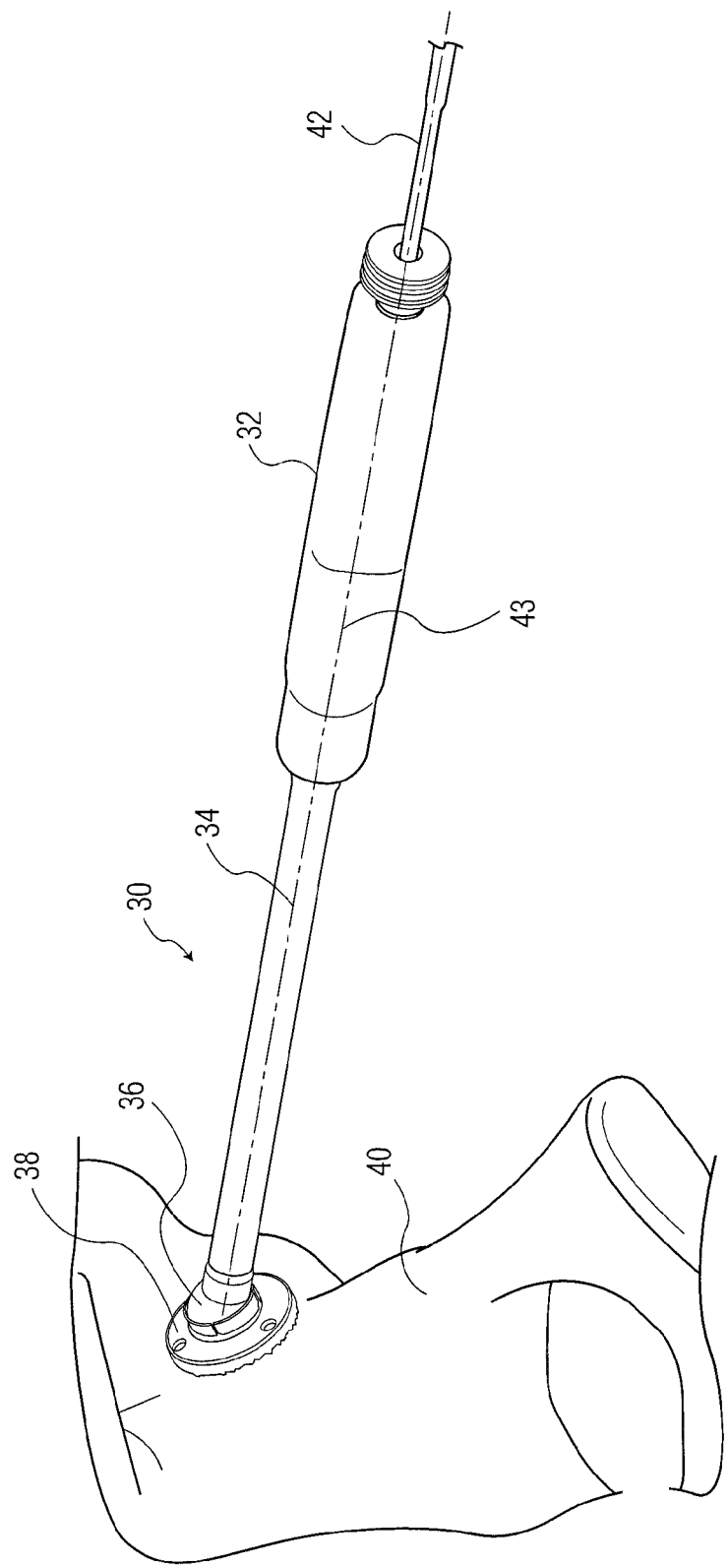
FIG. 3 is an isometric view of the bone screw insertion pusher system of the present invention used on a pelvic fracture.

Referring to FIG. 3, there is shown the bone screw insertion tool and pusher system of the present invention generally denoted as 30, which includes a handle portion 32, a cannulated shaft 34 extending along an axis 43. Tool 30 has a part-spherical leading end 36 integral with shaft 34, and a bone contacting plate 38 which has an angled inner surface so that it may pivot on leading end 36. As shown in FIG. 3, plate 38 is compressing a fracture on a pelvis 40. Handle 32 and shaft 34, as well as part-spherical end 36 are cannulated with a bore for receiving a drill 42, which may be used to drill a pilot hole in pelvis 40 so that a bone screw can be inserted across the fracture. The bore is also adapted to receive a screwdriver.

Figure 4A:
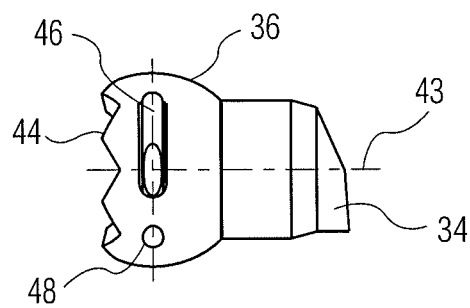
FIG. 4A is an elevation view of the leading end of the pusher of FIG. 3.
Figure 4B:
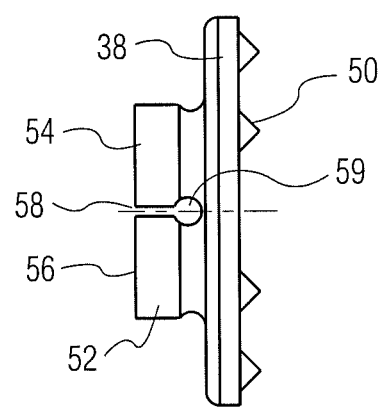
FIG. 4B is an elevation view of the pivot plate element capable of being mounted on the tip of FIG. 4A.
Figure 4C:
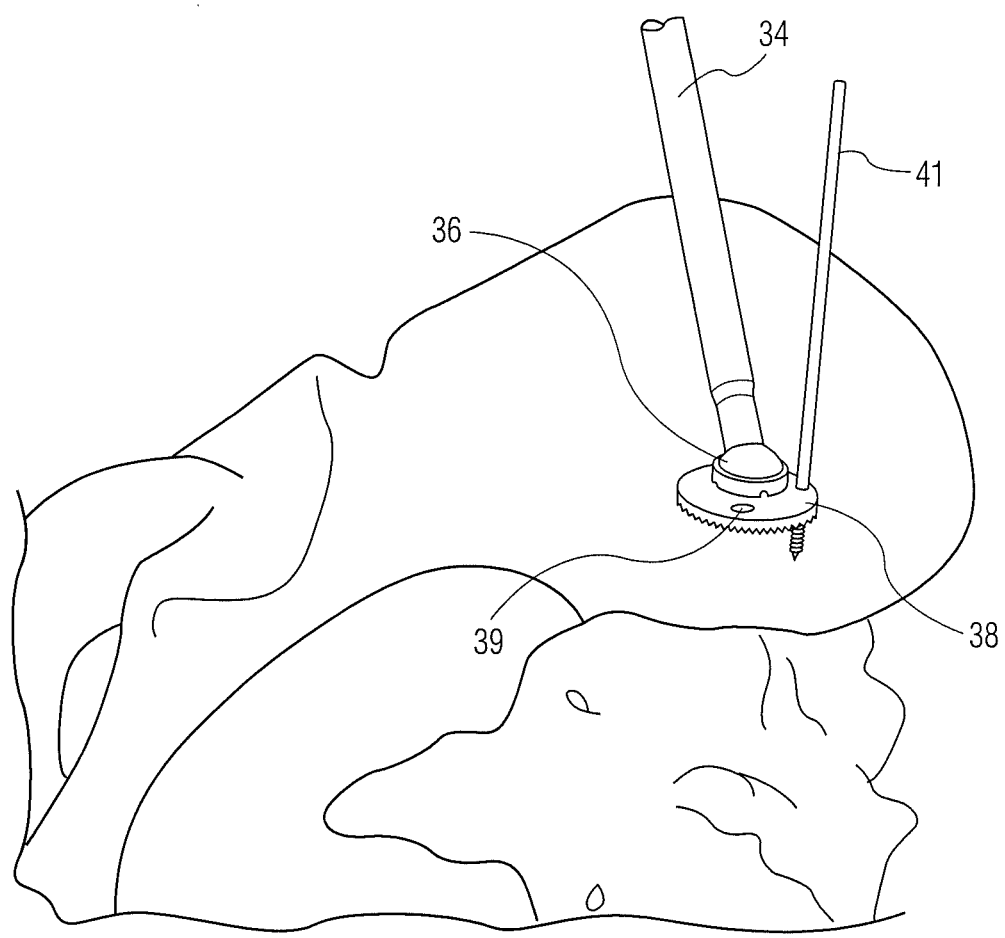
FIG. 4C shows the pusher of the present invention held in position by a Kirschner wire (K-wire)

Referring to FIG. 4A, there is shown an enlarged view of part-spherical leading end 36 of tool 30 with teeth 44 adapted to engage the bone. End 36 includes two slots 46 for receiving spring pins (not shown) which extend through each slot 46 and through a bore 48. While only one slot is shown in FIG. 4A, preferably slots 46 extend in parallel on opposite sides in a direction perpendicular to axis 43. The function of the spring pins will be described below. FIG. 4B shows an elevation view of plate 38 which has multiple teeth 50 which again engage the bone during fracture compression. Plate 38 includes a boss 52 having multiple spring sections two of which are shown in FIG. 4B as first and second sections 54 and 56. Sections 54, 56 may be sprung outwardly about slit 58 when engaging end 36 and thus may be mounted on end 36 but freely rotatable thereon. After assembly to end 36 plate 38 can rotate in all directions with respect to axis 43 of pusher 30 when plate 38 engages bone. Plate 38 includes three or more holes 39 each for receiving a K-wire 41 (see FIG. 4C). One K-wire 41 is shown in FIG. 4C which resists any lateral pressure applied by the surgeon.

Figure 5:
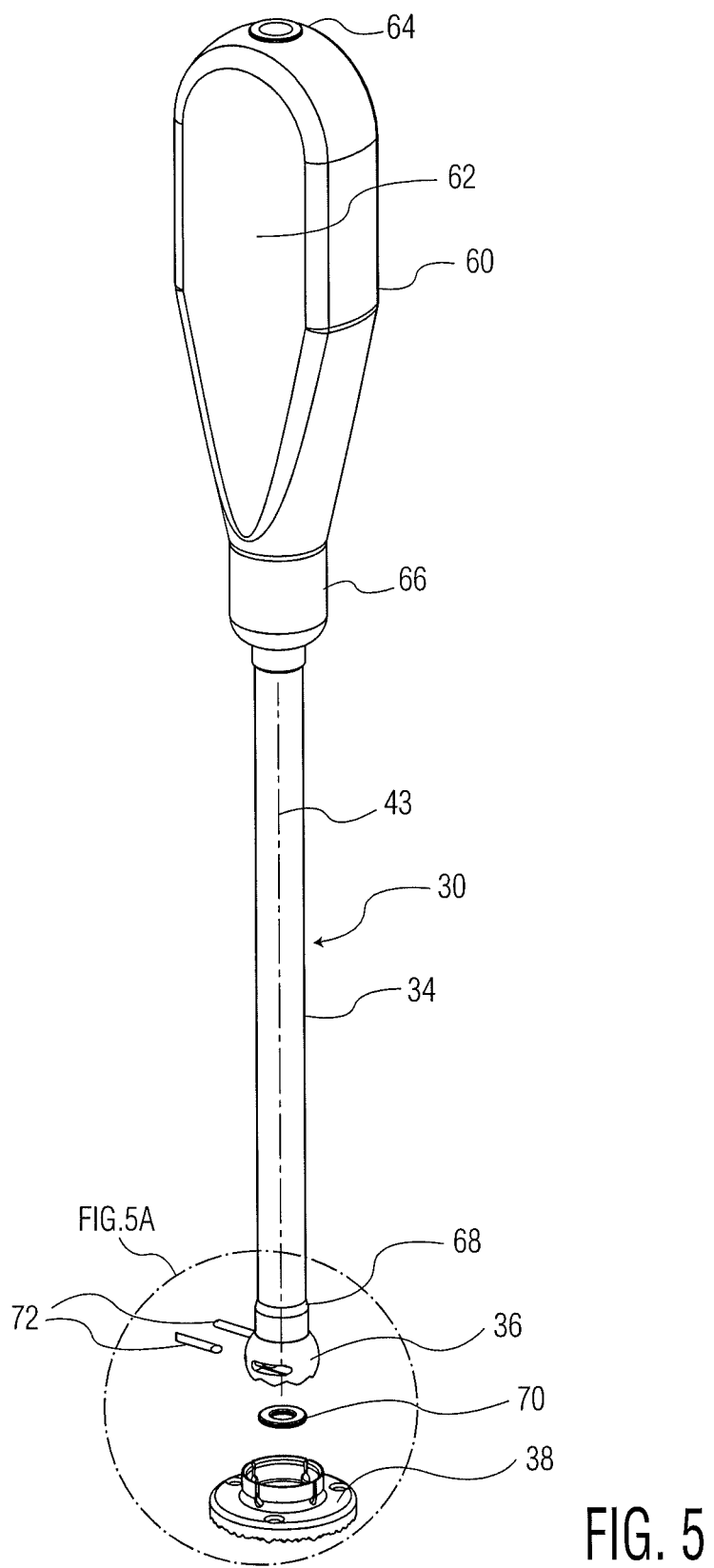
FIG. 5 is an exploded view of the system of FIGS. 3 through 4B showing a handle portion with flattened sides.

Referring to FIGS. 5 and 5A, there is shown the cannulated insertion or pusher tool 30, including a handle 60 which includes two flattened sides 62 which extend along parallel planes (only one side 62 is shown in FIG. 5). Handle 60 has a free end with an opening 64 providing an entrance into the cannulated bore 69 which extends along axis 43 (see FIG. 6). Handle 60 includes an end 66 engaging shaft 34, which in turn has an end 68 receiving part-spherical tip 36. Typically during manufacturing handle 60, shaft 34 and leading end 36 are manufactured as separate elements which may be fixed together such as by welding. A washer 70 is provided for engagement with a head of a bone screw which fixes the compressed fracture as will be discussed below. Washer 70 is held in place by a pair of preferably metal spring pins 72 which extend through slots 46 and bores 48 or opposite sides of axis 43 to maintain washer 70 within an opening in tool leading end 36 as is shown in FIG. 6.

Referring to 5A, there is shown an enlarged view of the end of the insertion tool or pusher of FIG. 5. It can be seen that plate 38 preferably has four spring sections 54, 55, 56, and 57 separated by four slits 58. Each slit has circular enlargements 59 at their bases to provide further resilience so that sections 54-57 of bone contacting plate 38 can snap onto the outer part-spherical surface of leading end 36. As seen in FIG. 5A, each pin 72 is inserted through a respective hole 48 into a respective slot 46. This is done prior to washer 70 being inserted onto an annular recessed surface 74 in the opening of tip 36 as shown in FIG. 6. Tip 36 has an end 37 which can include teeth 37a around the circumference. Referring to FIG. 5B one can eliminate plate 38 entirely and use the end 37 of shaft as the pusher surface. The teeth 37a keep the tool in position.

Figure 6:
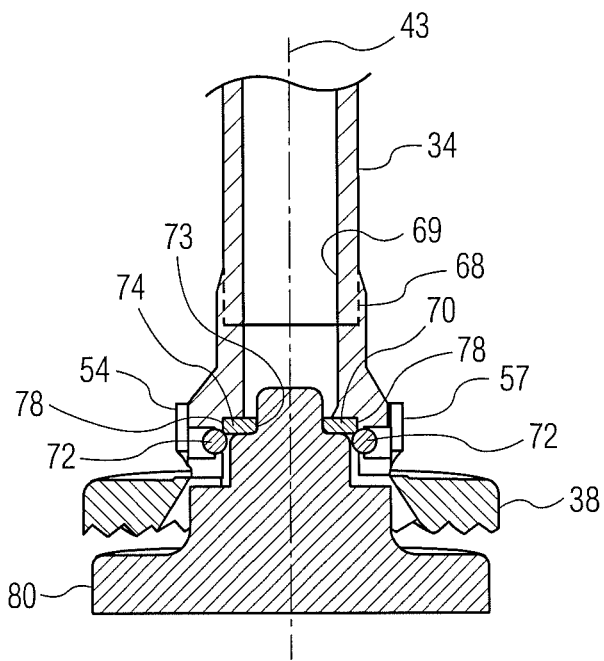
FIG. 6 is a cross-sectional view of the assembled leading end of the pusher system shown in FIG. 5A including a washer mounting tool.

Referring to FIG. 6, there is shown a cross-section of the assembled end of tool 30 with washer 70 mounted on the surface of annular recess 74 in the enlarged bore 78 within end 36. Tool end 36 has an enlarged bore 78 extending from a cannulated bore 69 of shaft 34. After assembly washer 70 engages annular surface 74 and is held in position by spring pins 72. Thus, annular surface 74 is spaced between slots 46 toward shaft 34 by the thickness of washer 70 so that each spring pin 72 can hold washer 70 in position on the annular surface 74.

Figure 6A:
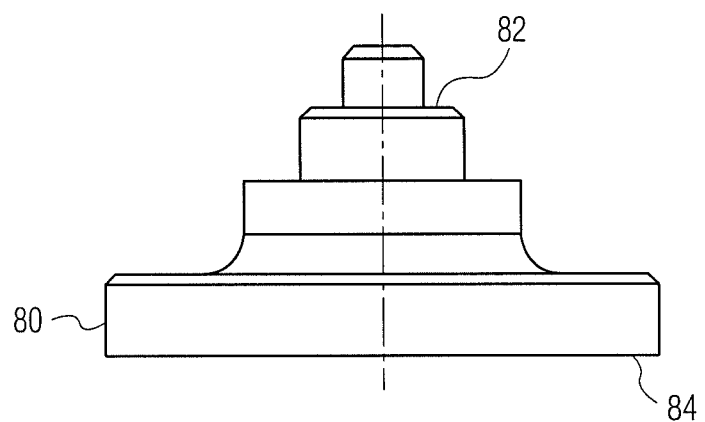
FIG. 6A is an elevation view of the washer mounting tool.

As shown in FIG. 6 an inner surface 76 of the spring pin 72 extends into an enlarged bore area 78 of end 36 to hold washer 70 in position. Washer 70 has an outer diameter 71 slightly less than the diameter of bore 78 and an inner diameter 73 slightly greater than the diameter of a bone screw shaft. A washer insertion tool 80 (also shown in FIG. 6A) can be used to place washer 70 on surface 74 after pins 72 have been mounted in tool end 36. The washer is placed on surface 82 of tool 80 while bottom surface 84 of tool 80 is located on a solid surface. Tool 30 with pins 72 mounted thereon is placed over tool 80 so that downward pressure via handle 60 will cause engagement between the top surface of the washer with the spring pins 72 causing them to expand sufficiently to allow washer 70 to be seated on surface 74 of tip 36. Once this occurs, screw insertion tool 30 may be removed from tool 80. Plate 38 may be mounted on shaft end 36 by placing plate 38 on a flat surface and snapping it onto end 36 by downward pressure on shaft 34.

Figure 7:
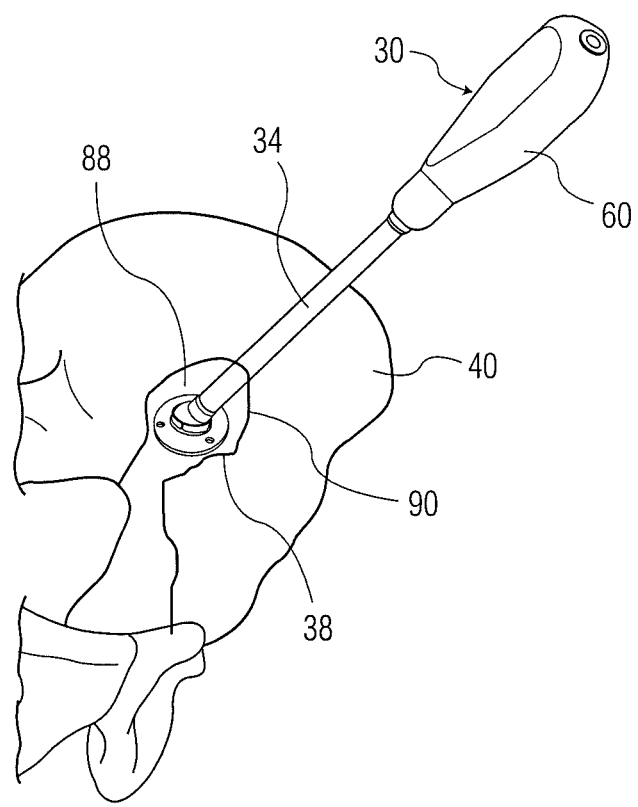
FIG. 7 is an isometric view showing the pusher system of the present invention utilized in compressing a bone fragment of a fractured pelvis.
Figure 8:
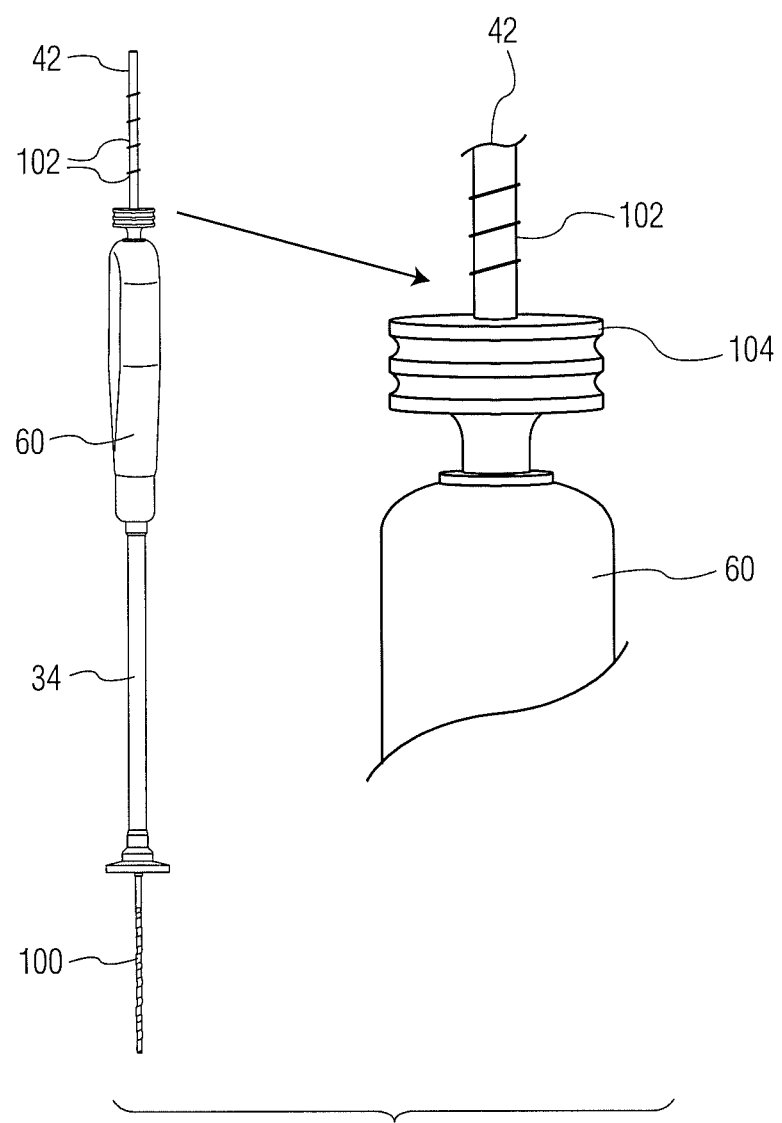
FIG. 8 is an isometric view of the pusher system of the present invention shown in FIGS. 3 through 7, including a drill including drill depth marking for drilling a pilot hole in bone.

Referring to FIG. 7, there is shown screw insertion tool 30 with plate 38 mounted thereon engaging a fragment of fractured bone 88 defining a fracture line 90 in pelvis 40. Preferably washer 70 is mounted in leading end 36 prior to drilling the pilot hole so that the tool 30 may remain in place throughout the procedure. Tool 30 is used to move bone fragment 88 into alignment with pelvic bone 40. Referring to FIG. 8, there is shown drill 42 extending along axis 43 through the cannulated bore 69 of shaft 34. Drill 42 has a leading end with a typical helically fluted drill 100 for drilling a pilot hole in bone 88. Drill 42 may include depth indicators 102 to aid the surgeon in determining the depth of the pilot hole drilled into bone 88. The indicators may be scribe lines spaced at 2 or 4 mm along the trailing end of drill 42. Since drill 42 is of a diameter smaller than a typical bone screw, a drill sleeve 104 having a tubular shaft (now shown) may be inserted into entrance 64 and down bore 69 of shaft 34 in order to center the drill 42 in bore 69. Sleeve 104 has an enlarged portion 105 to make it easier to insert and remove.

Figure 9:
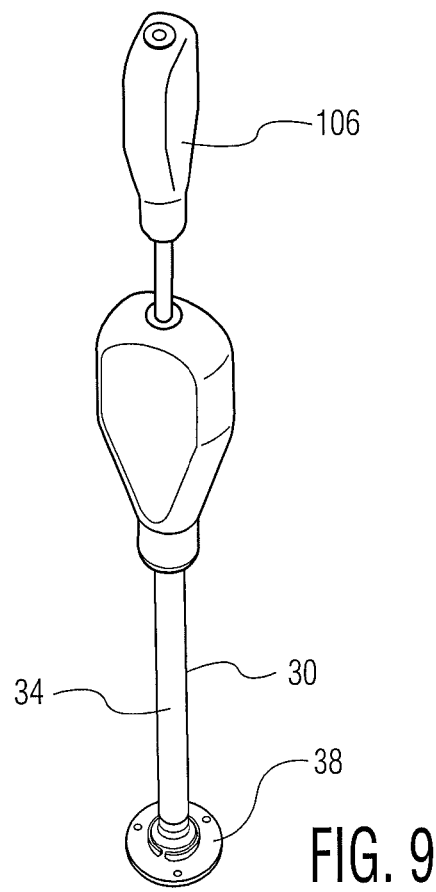
FIG. 9 shows the system of FIG. 8 with the drill removed and a screwdriver capable of driving a bone screw into bone mounted in the cannulated insertion tool.
Figure 10:
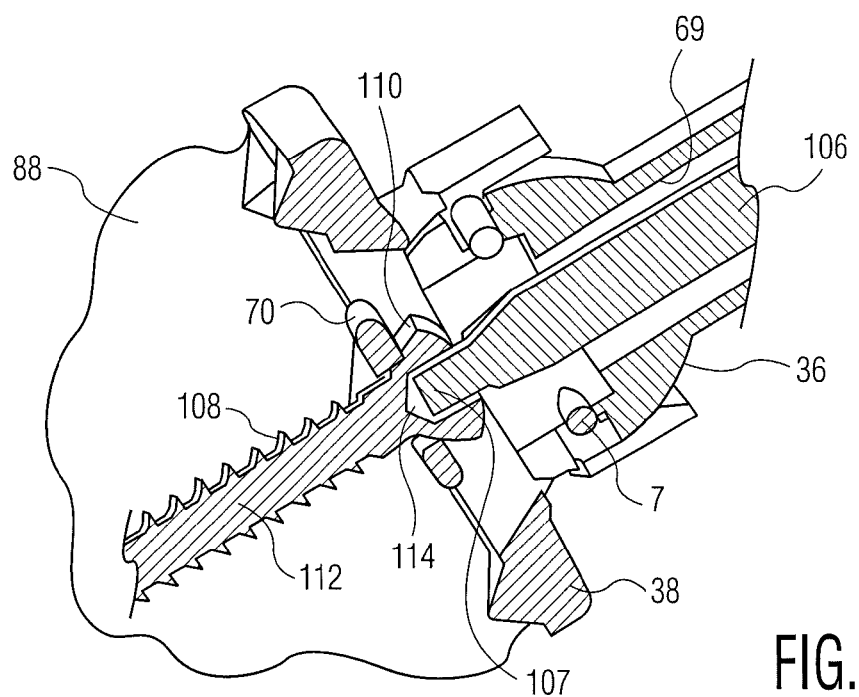
FIG. 10 is a cross-section of the leading end of the insertion tool of FIG. 9, including the screwdriver, washer and bone screw.

Referring to FIG. 9, there is shown tool 30 with a screwdriver 106 extending down cannulated bore 69 in shaft 34. Referring to FIG. 10, there is shown a cross-section of the leading end of pusher 30 with screwdriver 106 mounted within bore 69 and having a tip 107 engaging a bone screw 108 being inserted into bone 88. Screw 108 includes a head 110 and shaft 112. Head 110 may include a hexagonal recess for engaging a hex-shaped tip 107 of screwdriver 106. Obviously, any other drive system such as a Phillips-head or a Torx® drive can be used. Driver 106 is used to drive screw shaft 112 into bone until screw head 110 engages washer 70. As shown in FIG. 10, head 110 of screw 108 is of a sufficient diameter so that when it is inserted down bore 69 it is guided thereby and engages washer 70. By applying further torque to screwdriver 106, the bore 73 of spring elements 72 expand radially so that the screw and washer combination can move along axis 43 and seat on bone 88 thus fixing the fracture. Washer 70 allows for the forces developed by bone screw 108 to be spread over a larger area of bone and prevent crushing of softer bone. Once the screw and washer are inserted, the tool 30 is removed. The use of tool 30 thus allows for compressing the fracture, drilling the pilot hole, and inserting a bone screw and washer in a far simpler fashion that the prior art. Such an insertion can be done by a single surgeon. Specifically, the mounting of the washer 70 in the tip 36 prior to the operation allows insertion tool 30 to remain in place on the bone during the drilling and screw insertion steps. In addition there is no danger of the washer falling off the bone screw during use and becoming contaminated.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A bone screw insertion system comprising:
a bone screw having a head and a shaft;
an annular washer adapted to be mounted on the bone screw shaft;
an inserter having a longitudinally extending shaft with an axial bore therethrough for receiving the bone screw, the shaft having a first end with a washer retention means surrounding the inserter shaft bore, the washer retention means positioning the washer to receive the bone screw shaft; and
wherein the inserter shaft first end has an enlarged open recessed surface communicating with the shaft bore defining a seat for receiving the washer and having a resilient spring element for retaining the washer mounted thereon spaced towards the shaft leading end from the seat.

2. The bone screw insertion system as set forth in claim 1 further comprising a washer loading device having a portion with an annular surface for supporting the washer, the loading device capable of expanding the resilient spring element upon movement into the enlarged open recessed surface of the inserter shaft.

3. The bone screw insertion system as set forth in claim 1 wherein the first end of the inserter shaft having a surface having teeth thereon for contacting bone.

4. The bone screw insertion system as set forth in claim 1 wherein the inserter shaft includes a handle spaced along the inserter shaft away from the first end.

5. The bone screw insertion system as set forth in claim 1 wherein the inserter shaft first end has a part-spherical outer surface with a bone contacting plate mounted on the first end part-spherical outer surface, the plate having a bore with an angled surface which is rotatable on the part-spherical outer surface.

6. The bone screw insertion system as set forth in claim 1 wherein the inserter first end comprises a first and second crossbores extending along parallel first and second axis generally perpendicular to a longitudinal axis of the shaft, the first and second crossbores adjacent the washer seat.

7. The bone screw insertion system as set forth in claim 6 wherein a spring element extends through the first and second crossbores.

8. The bone screw insertion system as set forth in claim 7 wherein the spring elements are spring pins.

9. The bone screw insertion system as set forth in claim 1 wherein a plate is mounted on an outer surface at the first end of the inserter shaft, the plate having a bone contacting surface.

10. A bone screw system comprising:
a bone screw having a shaft and a head;
an insertion tool having a cannulated shaft for receiving the bone screw and a first end having an annular recessed area surrounding an open end of the cannulated shaft;

a plate having a surface thereon for contacting bone, the plate pivotally mounted on an outer surface of the first end of the insertion tool; and a driver for pushing the bone screw down the cannulated insertion tool shaft and driving it into a bone.

11. The bone screw insertion system as set forth in claim 10 further comprising an annular washer having an aperture for receiving the bone screw shaft, the washer mounted in the annular recessed area surrounding the cannulated bore and a resilient spring element engaging the washer for maintaining the washer in the recessed area.

12. The bone screw insertion system as set forth in claim 10 wherein the plate bone contacting surface has teeth thereon.

13. The bone screw insertion system as set forth in claim 10 wherein the insertion tool first end has a bone contacting surface having teeth thereon.

14. The bone screw insertion system as set forth in claim 11 further comprising a washer loading device having a portion with an annular surface for supporting the washer, the loading device capable of expanding the resilient spring element upon movement into an enlarged open bore at the first end of the insertion tool shaft.

15. The bone screw insertion system as set forth in claim 10 wherein the insertion tool shaft first end has a part-spherical outer surface and the bone contacting plate is mounted on the first end part-spherical outer surface, the bone contacting plate having an angled inner surface which is rotatable on the part-spherical outer surface.

16. The bone screw insertion system as set forth in claim 11 wherein the insertion tool first end comprises a first and second crossbores extending along parallel first and second axis generally perpendicular to a longitudinal axis of the shaft, the first and second crossbores adjacent the washer seat.

17. The bone screw insertion system as set forth in claim 16 wherein a spring element extends through the first and second crossbores.

18. The bone screw insertion system as set forth in claim 17 wherein the spring elements are cylindrical spring pins.

19. A method for inserting a bone screw into bone comprising:

obtaining a bone screw insertion system comprising:

a bone screw having a shaft and a head;

an insertion tool having a cannulated shaft for receiving the bone screw and a first end having a flat recessed area surrounding an open end of the cannulated shaft;

a driver for pushing the bone screw down the cannulated shaft and driving it into a bone;

inserting a washer onto the recessed area of the insertion tool;

compressing a bone fracture with the insertion tool shaft first end;

drilling a hole in the bone with a drill extending through the cannulated shaft while the bone fracture is compressed;

inserting the bone screw through the insertion tool cannulated shaft into the drilled hole while maintaining the compression;

driving the bone screw shaft into the bone with the driver; and picking up the washer with the bone screw head prior to fully driving the bone screw into the bone.

20. A bone screw insertion system comprising:

a bone screw having a head and a shaft;

an annular washer adapted to be mounted on the bone screw shaft;

an inserter having a longitudinally extending shaft with an axial bore therethrough for receiving the bone screw, the shaft having a first end with a washer retention means surrounding the inserter shaft bore, the washer retention means positioning the washer to receive the bone screw shaft; and wherein the inserter shaft first end has a part-spherical outer surface with a bone contacting plate mounted on the first end part-spherical outer surface, the plate having a bore with an angled surface which is rotatable on the part-spherical outer surface.

21. A bone screw insertion system comprising:

a bone screw having a head and a shaft;

a flat annular washer adapted to be mounted on the bone screw shaft, the flat annular washer having a single constant diameter bore therethrough, the annular washer bore diameter corresponding in size to the diameter of the bone screw shaft; and an inserter having a longitudinally extending shaft with an axial bore therethrough for receiving the bone screw, the shaft having a first end with a washer retention means surrounding the inserter shaft bore, the washer retention means positioning the flat annular washer to receive the bone screw shaft.

22. The bone screw insertion system as set forth in claim 21 wherein the inserter shaft first end has an enlarged open recessed surface communicating with the shaft bore defining a seat for receiving the washer and having a resilient spring element for retaining the washer mounted thereon spaced towards the shaft leading end from the seat.

23. The bone screw insertion system as set forth in claim 21 further comprising a washer loading device having a portion with an annular surface for supporting the washer, the loading device capable of expanding the resilient spring element upon movement into the enlarged open recessed surface of the inserter shaft.

* * * * *